(12) United States Patent  
Matsuzaki et al.

(10) Patent No.: US 7,501,633 B2
(45) Date of Patent: Mar. 10, 2009

(54) RADIOLOGICAL IMAGING APPARATUS AND TRANSMISSION IMAGING METHOD

(75) Inventors: Kazuki Matsuzaki, Hitachi (JP); Keiji Kobashi, Mito (JP); Yuichi Morimoto, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/560,546

(22) Filed: Nov. 16, 2006

(65) Prior Publication Data
US 2007/0135702 A1  Jun. 14, 2007

(30) Foreign Application Priority Data
Nov. 17, 2005  (JP)  ............... 2005-332290

(51) Int. Cl.
*G01T 1/164*  (2006.01)
(52) U.S. Cl. .................................. 250/363.03
(58) Field of Classification Search ............ 250/363.01, 250/363.02, 363.03, 363.04, 363.05, 363.06, 250/363.07, 363.08, 363.09, 363.1, 369; 378/9
See application file for complete search history.

(56) References Cited

U.S. PATENT DOCUMENTS

| 5,608,221 | A  | * | 3/1997  | Bertelsen et al. | ....... | 250/363.03 |
| 5,834,779 | A  | * | 11/1998 | Shao et al.      | .........| 250/363.03 |
| 6,040,580 | A  |   | 3/2000  | Watson et al.    |         |            |
| 6,171,243 | B1 | * | 1/2001  | Gagnon et al.    | ........| 600/431    |
| 6,528,793 | B1 | * | 3/2003  | Chen et al.      | .........| 250/363.03 |
| 6,965,661 | B2 |   | 11/2005 | Kojima et al.    |         |            |
| 6,976,784 | B2 |   | 12/2005 | Kojima et al.    |         |            |

| 2003/0146388 | A1 | 8/2003  | Wainer       |
| 2004/0213371 | A1 | 10/2004 | Bruder et al.|
| 2005/0135550 | A1 | 6/2005  | Man et al.   |

FOREIGN PATENT DOCUMENTS

| DE | 10046352      |   | 3/2001  |
| DE | 10302567      |   | 8/2004  |
| GB | 2022356   A   | * | 12/1979 |
| JP | 09-264961     |   | 10/1997 |
| JP | 10-295682     |   | 11/1998 |
| JP | 2001-099937   |   | 4/2001  |
| JP | 2003-057348   |   | 2/2003  |
| JP | 2003-079614   |   | 3/2003  |

OTHER PUBLICATIONS

Zaidi, Habib et al, "Determination of the Attenuation Map in Emission Tomography", Journal of Nuclear Medicine, vol. 44, No. 2, Feb. 2003, pp. 291-315.

* cited by examiner

*Primary Examiner*—David P Porta
*Assistant Examiner*—Kiho Kim
(74) *Attorney, Agent, or Firm*—Mattingly, Stanger, Malur & Brundidge, PC (57) ABSTRACT

A radiological imaging apparatus includes an imaging apparatus having an opening for insertion of a bed thereinto, and an attenuation correction data creating device. The imaging has a plurality of radiation detectors disposed around the opening and a plurality of gamma ray generation units residing between the opening and the radiation detectors disposed at a position nearest to the opening and being placed in a longitudinal direction of the bed. Each γ-ray generation unit has γ-ray sources of single photon emission nuclear species and is arranged to externally radiate a γ-ray alternately from either one of the γ-ray generators toward the opening. The data creator prepares attenuation correction data based on a detection signal as output from the radiation detector due to the incoming radiation of γ-rays from the γ-ray generator.

4 Claims, 9 Drawing Sheets

RADIOLOGICAL IMAGING APPARATUS AND TRANSMISSION IMAGING METHOD

FIELD OF THE INVENTION

The present invention relates to a radiological imaging apparatus for nuclear medicine diagnosis which performs transmission imaging using an external radiation source(s) and a transmission imaging method adaptable for use therewith.

DESCRIPTION OF THE RELATED ART

Radiological imaging apparatuses typically include gamma cameras, single photon emission computed tomography (SPECT) apparatus, and positron emission tomography (PET) apparatus.

In medical inspection using such readiological imaging apparatus, a radiopharmaceutical which contains therein a material having its nature of cumulating at a specific region is administered or doped into an object to be inspected, such as the body of a patient or examinee. A radiation detector or detectors are used to detect gamma (γ) rays as radiated from affected part of the examinee due to the radiopharmaceutical cumulated at such part. The γ-rays as emitted from the examinee's affected part have a specific energy peak: in the case of inspection using PET apparatus, a radiopharmaceutical of about 511 keV is used; in the case of inspection using SPECT apparatus, a radiopharmaceutical of about 100 keV is used. The radiological imaging apparatus is operatively responsive to receipt of a detection signal as output from the radiation detector that detected the γ-rays, for creating a tomographic image (to be referred to as "functional image" hereinafter) which includes an image of the radiopharmaceutical's cumulated part. This is called the emission imaging, also known as emission measurement.

The emission imaging typically includes two-dimensional (2D) imaging and three-dimensional (3D) imaging. The 2D imaging is a technique for performing image pickup by providing a septum between detectors so that the detection sensitivity in the axial direction of an imaging apparatus becomes uniform while at the same time enabling suppression of the influence of scattered radiation. However, the sensitivity of the entire imaging apparatus is low so that a time taken to collect data necessary for function image creation becomes longer. On the other hand, the 3D imaging without the use of septa is such that the detection sensitivity of the entire imaging apparatus is high so that the time taken to collect data necessary for the function image creation becomes shorter, although it is encountered with problems including the difficulty in keeping uniform the detection sensitivity in the axial direction of the imaging apparatus and the risk as to unwanted mixture of noises due to scattered rays and random coincidence. In recent years, the 3D imaging is becoming more important because of the requirement for improvement in throughputs.

The γ-rays to be emitted from an examinee are attenuated (absorbed) upon transmission through his or her body. In order to retain the quantitatively in the inspection using the radiological imaging apparatus, it becomes important to evaluate the γ-ray's attenuation quantity (absorption amount) within the body and also to correct based on such evaluation the γ-ray attenuation during emission measurement—i.e., attenuation correction or absorption correction. Measurement for collection of the data required for such attenuation correction or "transmission data" is called the transmission imaging, also known as transmission measurement. The transmission imaging uses an external gamma ray source (referred to hereinafter as external radiation source) as disposed between the examinee and the radiation detector: a collection method of the transmission data is different depending upon the type of such external radiation source. Examples of the external radiation source are a rod-shaped radiation source using $^{68}$Ge—$^{68}$Ga (germanium 68-gallium 68) that is a positron nuclear species and a point source of radiation using $^{137}$Cs which is a single photon emission nuclear species.

The rod-like radiation source of $^{68}$Ge—$^{68}$Ga radiates a pair of γ-rays having an energy of 511 keV in a direction of 180°. In the transmission imaging using the rod radiation source, either one of the paired γ-rays as emitted from the rod radiation source passes through the body of an examinee and is then detected by a radiation detector while preventing the other γ-ray from penetrating the examinee's body for detection by another radiation detector. Based on respective detection signals as output from the radiation detectors that detected the γ-rays, simultaneous or "coincidence" counting is performed to thereby collect the transmission data between such detectors. In the inspection using the PET apparatus (i.e., PET inspection), a post-injection method is employed which has the steps of doping a radiopharmaceutical in an examinee, and, after the elapse of a prespecified length of time required for the cumulation of such radiopharmaceutical to an internal organ being inspected (e.g., 30 to 60 minutes), continuously performing transmission imaging and emission imaging operations. In this case, since both the γ-ray as emitted from the $^{68}$Ge—$^{68}$Ga rod radiation source and the γ-ray to be emitted due to the radiopharmaceutical that has cumulated within the examinee's body are at 511 keV, unwanted data mixture can occur between the transmission and the emission, resulting in a likewise increase in noises. Additionally, the one γ-ray that is emitted from the rod radiation source does not pass through the object being inspected and behaves to directly hit the radiation detector as disposed at a location adjacent to the bar radiation source. Consequently, such radiation detector gets higher in count rate, which leads to the presence of a limit to the emission intensity of such rod radiation source.

On the contrary, the point radiation source of $^{137}$Cs (cesium 137) has a shield for controlling a radioactive material and the irradiation direction of γ-rays and for shaping a γ-ray irradiation region (e.g., into a circular conic shape), and radiates γ-rays having an energy of 662 keV. In the transmission imaging using the point radiation source, the radiated γ-rays having its shaped irradiation form passes through the body of an examinee, followed by detection of such γ-rays at radiation detectors. PET apparatus is responsive to receipt of the position information of a γ-ray-sensed radiation detector(s) and the position information of an external radiation source(s), for collecting transmission data. In the case of using the $^{137}$Cs point radiation source while employing the post-injection method, the point radiation source-emitted γ-rays and the γ-rays to be radiated from the examinee's body are different in energy from each other, so this approach offers an advantage as to reduced data mixture between the transmission and the emission. In addition, the point radiation source limits the irradiation range of γ-rays at a shielding vessel and collimator to thereby ensure that no γ-rays fall onto a radiation detector which is disposed in close proximity to the point radiation source whereby it is possible to increase the emission intensity of the point radiation source while enabling collection of transmission data less in statistics noises within a short length of time period. In this way, the transmission data may be improved in quality, resulting in improvement in functional image quality. From these viewpoints, the transmission imaging using point radiation sources is currently the major approach.

JP-A-9-264961 discloses therein a SPECT apparatus which comprises a single external radiation source having a shield for restriction of the irradiation region of a γ-ray as emitted from external point radiation source and a shutter that is provided at an opening of the shield for providing forward/backward driving in the horizontal direction. This Japanese patent bulletin JP-A-9-264961 teaches a technique for causing the shutter to open and close to thereby control the radiation start and interruption of γ-rays from the external radiation source. A radiation detector is placed at a location whereat it opposes the external radiation source and rotates together with the external radiation source in units of supported rotation steps. Transmission image pickup using such sole external radiation source becomes narrower in imaging field-of-view within the imagable range of an imaging apparatus. Additionally in transmission imaging with movement, an imaging time becomes longer.

U.S. Pat. No. 6,040,580 discloses therein a PET apparatus and SPECT apparatus with a plurality of point radiation sources being disposed along the length of a bed within an imaging apparatus. The PET apparatus and SPECT apparatus include a collimator which is provided between adjacent ones of the point radiation sources to thereby ensure that γ-rays emitted from these point sources fall onto the same radiation detector at a time. In such combination of the point radiation sources and collimators as taught by U.S. Pat. No. 6,040,580, an increase in radiation source intensity in order to shorten the imaging time brings a need to increase the thickness of each collimator; accordingly, increasing the intensity does not come without accompanying limits. Additionally, the PET apparatus and SPECT apparatus as taught by U.S. Pat. No. 6,040,580 are such that detectors are positioned at part of a ring, so the imaging field-of-view within the cross-section of an imaging device must be limited.

The transmission imaging using a sole point radiation source suffers from the narrowing of field-of-view along the length of the bed. In cases where all the regions to be inspected are incapable of being image-sensed at a time (for example, in entire body inspection for cancer check), image pickup is done by subdividing the to-be-inspected region into a plurality of portions with overlapping imaging areas while causing either the imaging or the bed to move. However, in the transmission imaging with movement, a need is felt to retain an increased overlapping width, which in turn requires an increased length of time for the whole-body transmission imaging. Alternatively in the brain functionality inspection and heart function check without the bed motion, it is required to perform the imaging of a target internal organ, such as brain or heart, at a single imaging position while letting the imaging or the bed stay motionless. Unfortunately, the point radiation source is inherently narrow in image pickup range, so it is difficult to achieve the imaging of every inspection object range (all parts of interest) at a time.

SUMMARY OF THE INVENTION

It is therefore an object of the present invention to provide a technique for achievement of a wide field of view while emitting a radiation ray from one of a plurality of point radiation sources used and to shorten a time required for transmission imaging.

To attain the foregoing object, a radiological imaging apparatus in accordance with one aspect of this invention includes an imaging apparatus with an opening being formed for insertion of a bed thereinto, and an attenuation correction data creation device. The imaging apparatus has a plurality of radiation detectors disposed around the opening and a plurality of gamma (γ) ray generation means residing between the opening and the radiation detectors which are placed at a position nearest to the opening and being disposed along the length of the bed. The plurality of γ-ray generation means respectively comprise γ-ray sources each being a single photon emission nuclear species and have an arrangement for alternately radiating a γ-ray from either one of the γ-ray generation means to its outside and toward the opening. The attenuation correction data creation device is operable to create attenuation correction data based on a detection signal as output from the radiation detectors due to incoming radiation of the γ-ray to be emitted from the γ-ray generation means.

In accordance with another aspect of this invention, a radiological imaging apparatus includes an imaging apparatus with an opening being formed for insertion of a bed thereinto, and an attenuation correction data creation device. The imaging apparatus has a plurality of radiation detectors disposed around the opening and a γ-ray generation unit which is a single photon emission nuclear species and which has a plurality of γ-ray sources that are disposed between the opening and the radiation detectors disposed nearest to the opening and a plurality of release windows for radiating γ-rays from the γ-ray sources toward the opening. The γ-ray generation unit has an arrangement for alternately radiating the γ-ray from either one of the release windows. The attenuation correction data creation device creates attenuation correction data based on a detection signal as output from the radiation detector due to incoming radiation of the γ-ray to be emitted from the γ-ray generation unit.

With the radiological imaging apparatus incorporating the principles of the invention, it is possible to achieve a wide field of view by using the point radiation sources and also to shorten the time required for the transmission imaging.

Other objects, features and advantages of the invention will become apparent from the following description of the embodiments of the invention taken in conjunction with the accompanying drawings.

BRIEF DESCRIPTION OF THE DRAWINGS

FIGS. 5A to 5C are diagrams pictorially showing arrangements of external point radiation sources and the point radiation source holding rotation shaft, wherein

FIGS. 6A and 6B are diagrams pictorially showing FOV in the case of two point sources of radiation being simply disposed, wherein

DETAILED DESCRIPTION OF THE INVENTION

Currently preferred embodiments of the invention will be described with reference to the accompanying drawings below.

Embodiment 1

A radiological imaging apparatus as one preferred embodiment of this invention will be described using some of the accompanying drawings. The imaging apparatus of this embodiment will be explained while taking as an example a positron emission tomography (PET) apparatus having two external radiation sources using a chosen single photon emission nuclear species, such as $^{137}$Cs (cesium 137).

Figure 11:
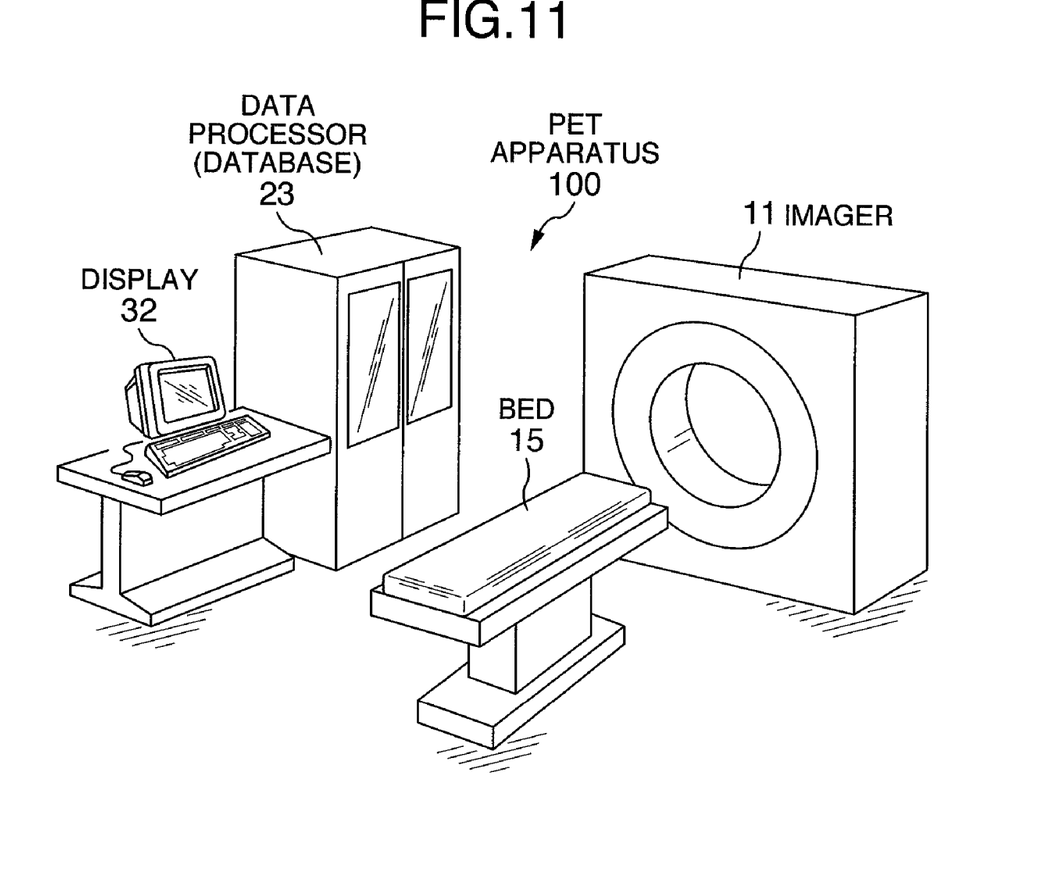
FIG. 11 is a plan view showing an arrangement of PET apparatus which is one preferred embodiment of this invention.
Figure 12:
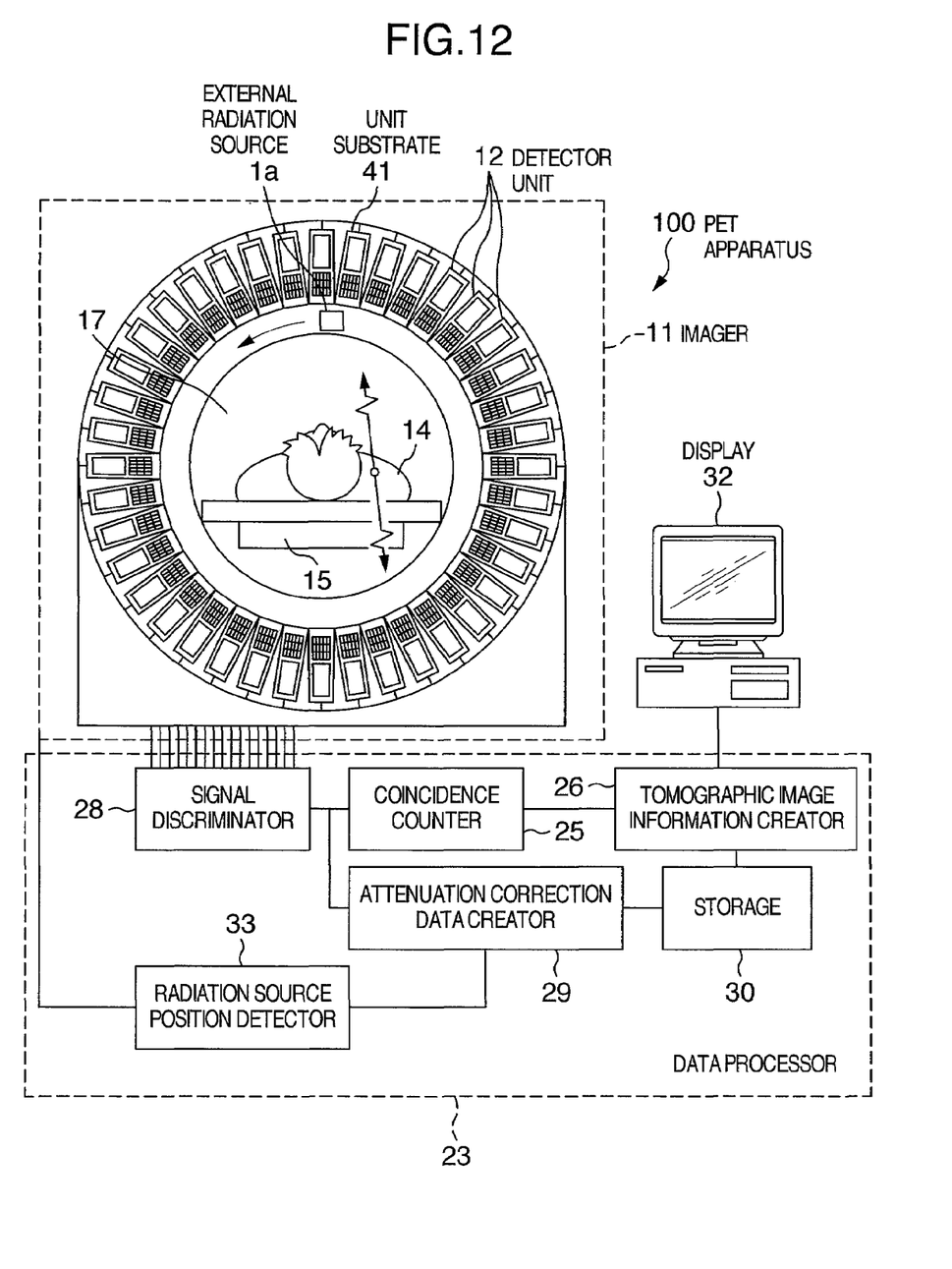
FIG. 12 is a diagram pictorially showing the PET apparatus shown in FIG. 11.

As shown in FIG. 11, the PET apparatus 100 includes an imaging apparatus 11, a bed (bunk) 15, a data processing apparatus 23 including a data accumulation device or database, and a display device 24. The data processor 23 has as shown in FIG. 12 a signal discrimination device 28, coincidence counter 25, tomographic image data creation device 26, transmission data processing device (attenuation correction data forming device) 29, storage device 30, and radiation source position detection device 33. The signal discriminator 28 is connected to the coincidence counter 25 and the attenuation correction data creator 29. The coincidence counter 25 is connected to the tomographic image information creator 26. The attenuation correction data creator 29 is coupled to the storage device 30. This storage device 30 is connected to the tomographic image information creator 26. The tomographic image information creator 26 is connected to the display device 32.

Figure 13:
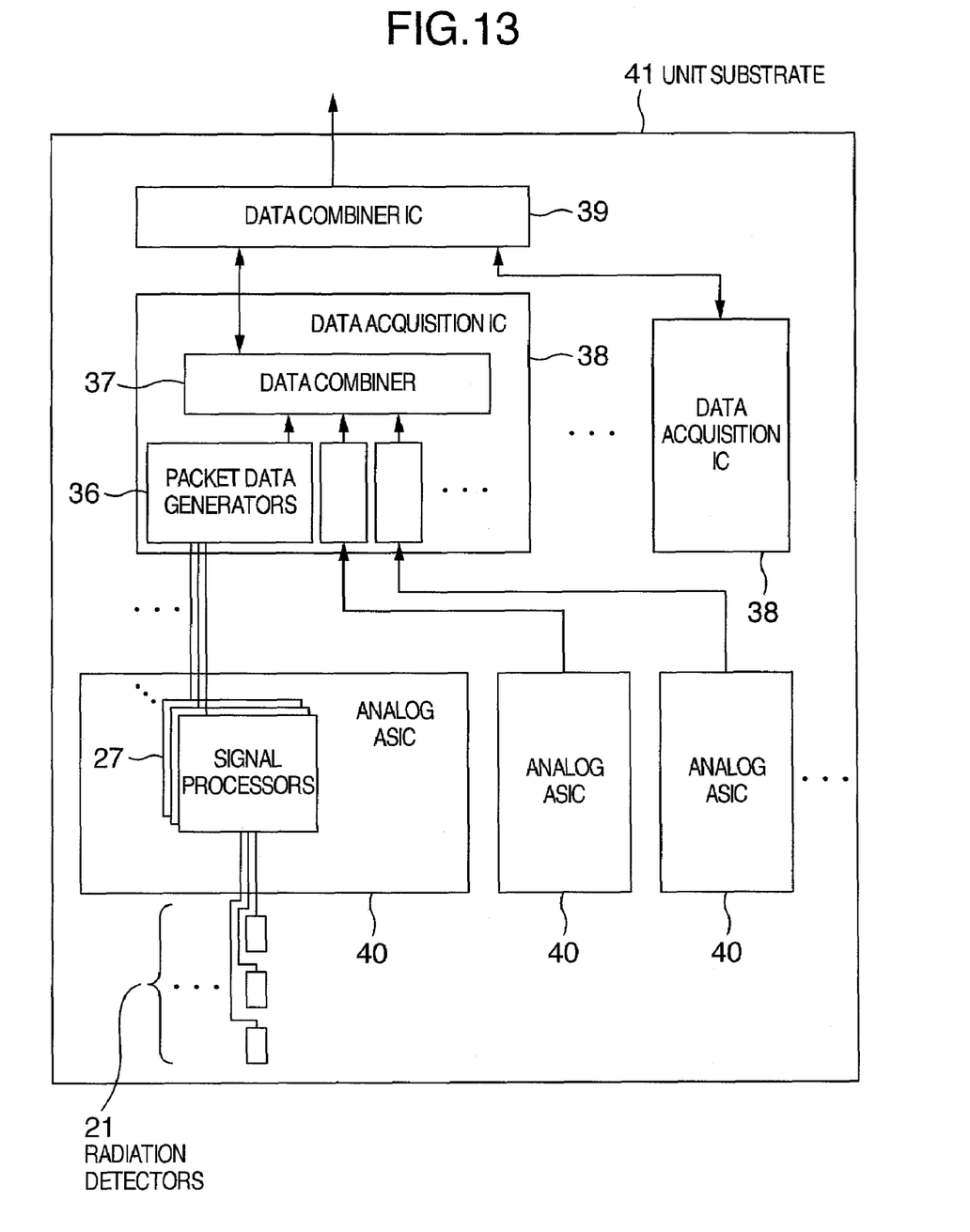
FIG. 13 is a configuration diagram showing a unit substrate shown in FIG. 12.

As shown in FIG. 12, the imaging apparatus 11 has a cylindrical opening (through-hole) 17 for permitting insertion of the bed 15 thereinto, with a plurality of detector units 12 being installed to surround this opening 17. The detector units 12 have a plurality of unit substrates 41 along the length of the bed 15. As shown in FIG. 13, each unit substrate 41 has a plurality of semiconductor radiation detectors 21, a plurality of analog application-specific integrated circuits (ASICs) 40, a plurality of data acquisition ICs 38, and a data combining or "synthesis" 1C 39. Each analog ASIC 40 has a plurality of signal processing devices 27. The data acquisition IC 38 has a plurality of packet data generation devices 36 and a data combining device 37. The radiation detectors 21 are placed around the opening 17 to surround the same. Radiation detectors 21 are also laid out along the length of the bed 15. More than two banks of radiation detectors 21 are disposed in a radial direction of the opening 17. The radiation detectors 21 are connected to separate signal processors 27, respectively. In other words, the signal processors 27 are provided in units of the radiation detectors 21. Multiple respective signal processors 27 are connected to the packet data generator 36. Packet data generators 36 are connected to the data combiner 37. Data combiners 37 are connected to the data combiner IC 39. This IC 39 is connected to the signal discriminator 28 as provided in the data processor 23.

Figure 1:
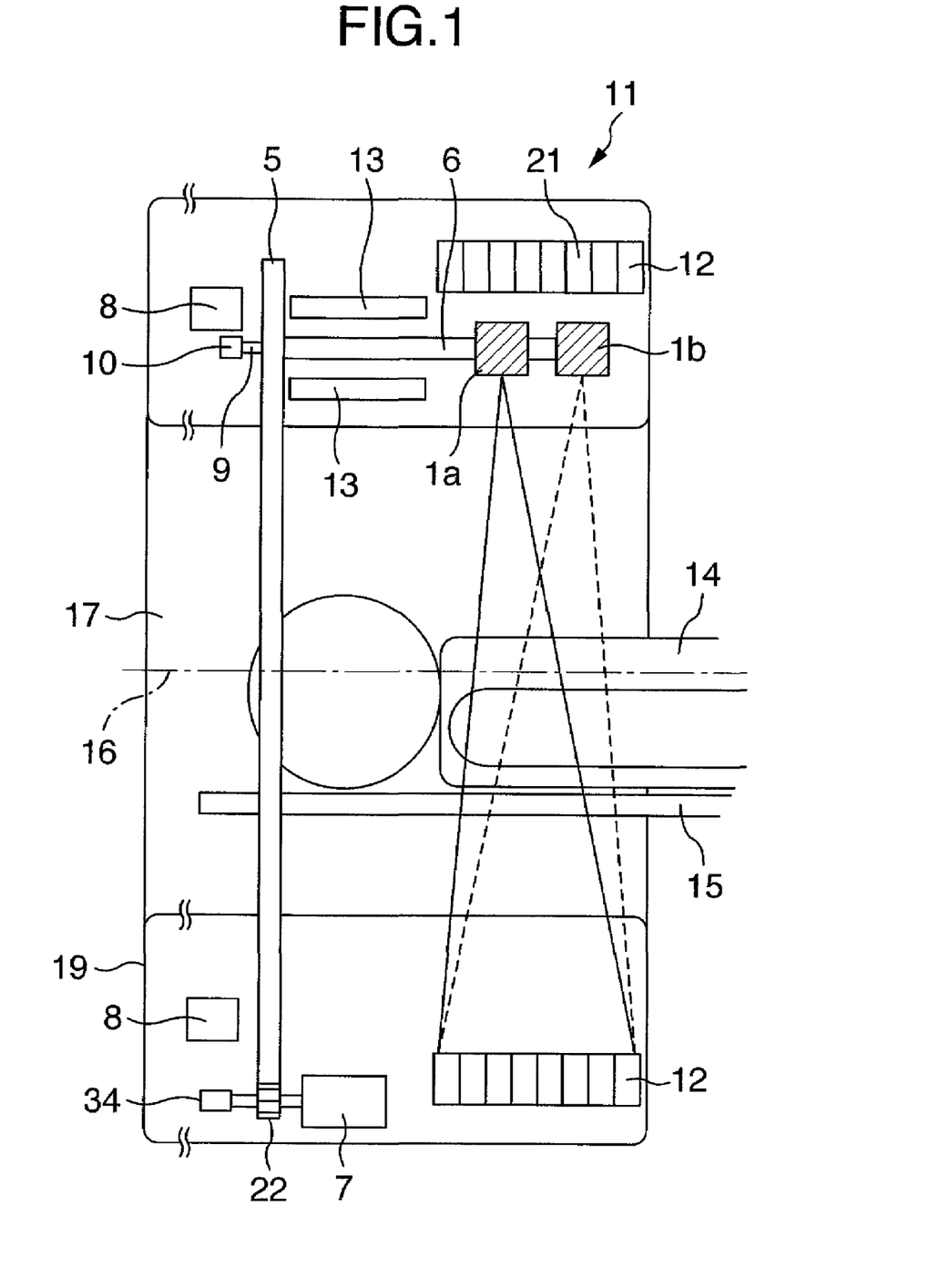
FIG. 1 is a configuration diagram showing a cross-sectional structure in the long-side direction of a bed of an imaging apparatus of PET apparatus which is one embodiment of the present invention.
Figure 4:
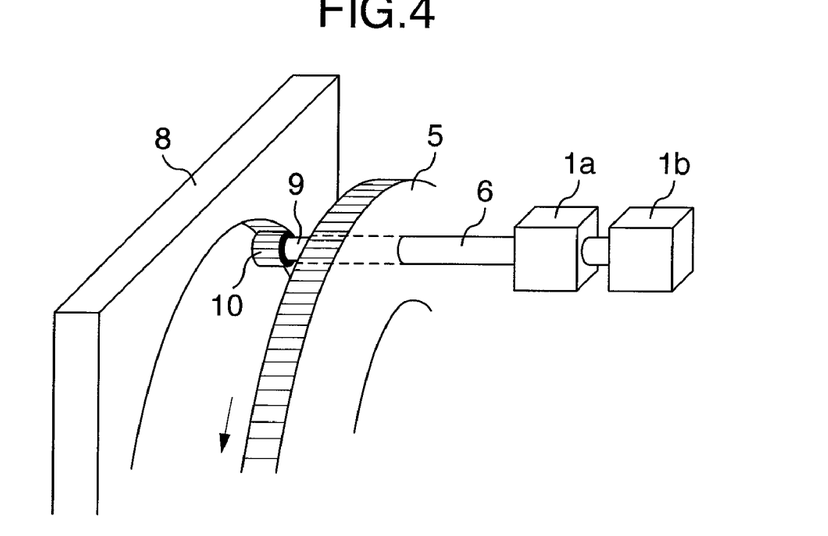
FIG. 4 is a diagram pictorially showing arrangements of an internal gear, a rotational ring and the point radiation source holding shaft.

Additionally as shown in FIG. 1, the imaging apparatus 11 has a casing 19 having its interior in which provided are a couple of external radiation sources 1a and 1b and a radiation shield vessel 13 plus a hollow circular rotational ring 5. An internal gear 8 which surrounds the circumference of the opening 17 and which has a rack formed therein is disposed inside of the casing 19 and is fixed to the casing 19 to thereby have no rotatability. The internal gear 8 is attached to the casing 19 while offering slidability in the long-side direction of the bed 15. The external radiation sources 1a-1b are placed between the opening 17 and the radiation detectors 21 that are disposed nearest to the opening 17. The external radiation sources 1a-1b are placed in parallel along the length of bed 15 and are supported by a radiation source housing supporting rod 6 that is fixed to the rotational ring 5. The radiation source housing support rod 6 has therein a radiation source holding rotational shaft 9. The radiation source holding rotational shaft 9 penetrates the rotational ring 5 and has a gearwheel 10 at its distal end. The gearwheel 10 is inserted into the internal gear 8 and is engaged with a rack as formed inside of the internal gear 8 (see FIG. 4). A rotation driving device 7 is disposed within the casing 19 and has an electric motor (not shown), a power transmission mechanism (not shown) and a gearwheel 22. The power transmission mechanism is coupled to the motor. The gearwheel 22 is attached to a rotation shaft of the power transmission mechanism. The gearwheel 22 is engaged with the rack as formed in the rotational ring 5. A rotation angle detection device 34 which is coupled to the rotation detector 7's rotation shaft and a rotation angle detector 35 that is coupled to the rotation shaft of the radiation source holding rotation shaft 9 are connected to the radiation source position detector 33, respectively.

Figure 3:
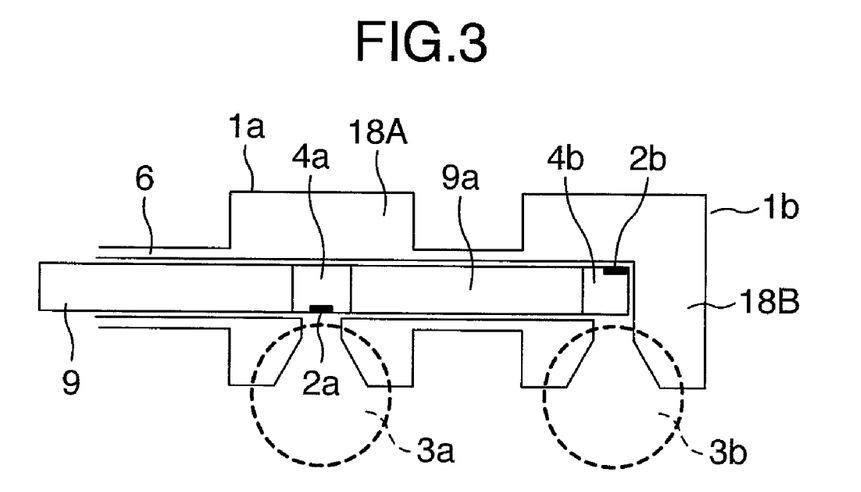
FIG. 3 is a diagram pictorially illustrating a cross-sectional structure of external point radiation sources of the PET apparatus shown in FIG. 1 in the axial direction of a point radiation source holding rotation shaft.

As shown in FIG. 3, the external radiation source 1a has a radiation source housing 18A, a transmission-use point source of radiation ($^{137}$Cs, to be referred hereinafter as "point radiation source") 2a and a shield 4a. The point radiation source 2a and shield 4a are placed inside of the radiation source housing 18A. The radiation source housing 18A has a radiation release window (radiation exit hole) 3a as formed therein, which is for shaping a gamma (γ) ray as emitted from the point radiation source 2a into a desired shape and for releasing resultant γ-ray toward the outside of the radiation source housing 18A. The radiation release window 3a is formed at a position for outward release of the γ-ray being emitted from the point radiation source 2a toward the opening 17. The radiation source housing 18A is a radiation shielding structure for shielding or blocking those γ-rays as externally emitted from those regions other than the radiation release window 3a. The radiation source housing 18A and the radiation source housing support rod 6 are structurally integrated together. The shield 4a is fixed to the radiation source holding rotational shaft 9 within the radiation source housing 18A. The point radiation source 2a is installed at a surface portion of the shield 4a.

The external radiation source 1b has a radiation source housing 18B, point radiation source 2b and shield 4b. The point radiation source 2b and shield 4b are disposed within the radiation source housing 18B having a radiation release window 3b formed therein, which is similar to the radiation release window 3a. The radiation source housing 18B is coupled to the radiation source housing 18B. The shield 4b is attached to the shield 4a by way of a rotation shaft 9a which is placed within the radiation source housings 18A and 18B. The point radiation source 2b that is provided at a surface portion of the shield 4b is placed at a position which is 180°-shifted relative to the point radiation source 2a in the rotation direction of the radiation source holding rotational shaft 9.

Below is an explanation as to transmission imaging and transmission imaging methods in the illustrative embodiment. In this embodiment, heart function inspection of a patient or examinee is taken as an example thereof for explanation of a case where it employs an emission/transmission simultaneous image pickup method (ET coincidence imaging method) which performs the emission imaging and the transmission imaging simultaneously.

Prior to execution of PET inspection, a radiopharmaceutical (e.g., $^{18}$F) is pre-doped by an injector into an object to be inspected, such as the body of an examinee 14. The examinee 14 waits ready for a certain time (30 to 60 minutes) until the PET-use chemical that was doped into the examinee 14 diffuses in his or her body and then is accommodated in heart muscle that is a portion to be inspected and is next cumulated therein. Thereafter, let the examinee 14 lie on the bed 15.

An operator manually operates a button as provided on an operation console (not shown) so that an inspection start signal is output to a supervisory system control unit (not shown). Upon input of the inspection start signal, the system controller outputs information as to an inspection target range of the examinee 14 and a bed movement start signal to a bed motion control unit (not shown). This bed motion controller is responsive to receipt of the start signal, for moving the bed 15 based on the input information in such a way that the heart of examinee 14 to be inspected enters the γ-ray detection area (opening 17) of the PET apparatus 100. The system controller also outputs a radiation source positioning signal to a straightforward or "linear" driving device (not shown). In responding to this signal, the linear driver causes the radiation source housings 18A-18B, rotational ring 5, radiation source housing support rod 6 and external radiation sources 1a-1b to move together in an axial direction of the opening 17 (i.e., in a longitudinal direction along the length of bed 15). Owing to such movement, the external radiation sources 1a-1b are taken out of the radiation shield vessel 13 and then placed at prespecified locations. In this state, transmission imaging and emission imaging get started.

Figure 5A:
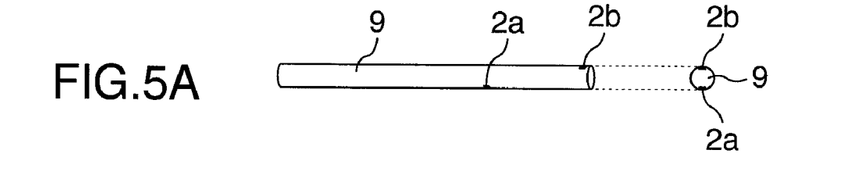
FIG. 5A is a pictorial representation showing layout positions of the point radiation sources.
Figure 5B:
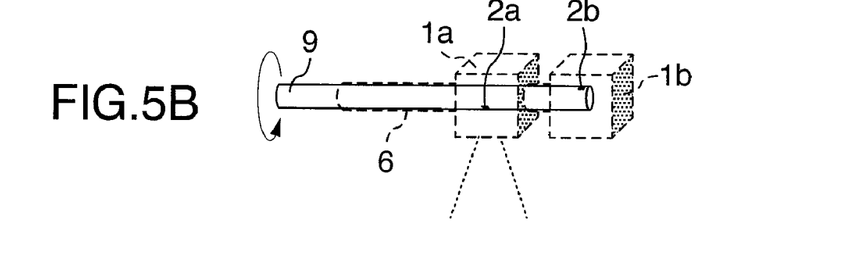
FIG. 5B is a pictorial diagram showing layout positions of the point radiation sources in case an external radiation source 1a emits a γ-ray.
Figure 5C:
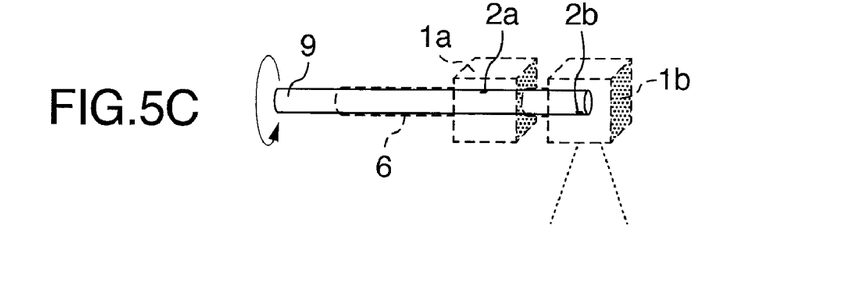
FIG. 5C is a pictorial diagram showing layout positions of the point radiation sources when an external radiation source 1b emits a γ-ray.

An explanation will first be given of the transmission imaging. The system controller closes an open/close device (not shown) which is connected to a power supply as coupled to the motor of the rotation driver 7. The supply of a current causes the motor to rotate, resulting in transmission of its rotation force to the gearwheel 22 via the power transmission mechanism. Owing to the rotation of the gearwheel 22, the rotational ring 5 rotates around the opening 17 in a direction indicated by arrow (in FIG. 4). By the rotation of rotational ring 5, the external radiation source 1a, 1b and the radiation source housing support rod 6 and others circulate around the circumference of opening 17, that is, the examinee 14. Further, by the rotation of rotational ring 5, the gearwheel 10 being engaged with the rack of internal gear 8 rotates, causing the radiation source holding rotational shaft 9 and point radiation sources 2a-2b plus shields 4a-4b to rotate in a direction of arrow as indicated in FIGS. 5B and 5C. When the point radiation source 2a is at a position other than the radiation release window 3a, the shield 4a blocks γ-rays being radiated from the point radiation source 2a to thereby prevent irradiation toward the opening 17 through the radiation release window 3a. When the point radiation source 2b is at a position other than the radiation release window 3b, the shield 4b shields γ-rays being emitted from the point radiation source 2b to thereby prevent irradiation toward the opening 17 from the radiation release window 3b. Furthermore, since the point radiation sources 2a-2b are disposed at 180°-shifted positions respectively as stated previously (see FIG. 5A), the rotation of them results in the γ-ray being released out of an external radiation source which is either one of the external radiation sources 1a and 1b. The γ-rays are alternately emitted from either one of the external radiation sources 1a-1b.

After having passed through the examinee 14, these γ-rays are detected by more than two radiation detectors 21 which are placed in a circumferential direction with a radiation detector 21 being as the center, which resides on extension lines of respective straight lines that couple together the axis center of the opening 17 and the point radiation source 2a, 2b. These radiation detectors 21 output to separate associated signal processors 27 γ-ray detection signals (namely, transmission signals) corresponding to the energies of such γ-rays. In response to receipt of the transmission signals as output from respective radiation detectors 21, the signal processors 27 generate timing signals for specifying detection time points of the γ-rays. The timing signals generated are sent forth toward a packet data generator 36. The packet data generator 36 determines based on the timing signals a γ-ray detection time point (τ) to thereby identify a detector ID (i.e., ID for judging the radiation detector 21) N. In addition, the signal processors 27 generate based on the transmission signals the wave height value information of γ-rays, which will be sent to the packet data generator 36. The packet data generator 36 converts the wave height value information into digital pulse height value data (E). The packet data generator 36 adds the pulse height value data (E) to the time information (τ) and detector ID (N) to thereby produce packet data (N, τ, E). The packet data (N, τ, E) will then be transferred to the signal discriminator 28 via the data combiner 37 and data combiner IC 39.

Next, the emission imaging will be explained. From the body of the examinee 14 lying on the bed 15 which is inserted into inside of the opening 17, a pair of γ-rays of 511 keV as generated due to the radiopharmaceutical are emitted in almost every direction. Each ray of such paired γ-rays is sensed by respective radiation detectors 21 that are placed in 180° opposite directions. These radiation detectors 21 output respective γ-ray detection signals (say, emission signals) corresponding to such γ-rays' energies, which signals are input to their corresponding signal processors 27. In responding to the emission signals as output from respective radiation detectors 21, the signal processors 27 generate timing signals for identification of a γ-ray detection time point. The timing signals thus generated are passed to the packet data generator 36. The packet data generator 36 determines based on the timing signals the γ-ray detection time (τ) and identifies detector ID (ID for discrimination of radiation detector 21). In addition, the signal processors 27 generate based on the transmission signals the wave height information of γ-rays, which will be transferred to the packet data generator 36. The packet data generator 36 converts the wave height information into digital pulse height value data (E). The packet data generator 36 adds the pulse height value data (E) to the time information (τ) and detector ID (N) to thereby generate packet data (N, τ, E). The packet data (N, τ, E) will then be sent to the signal discriminator 28 via the data combiner 37 and data combiner IC 39. Additionally, let the position information of radiation detector 21 be first position information.

The signal discriminator 28 is responsive to receipt of the packet data having the pulse height value data of a first setup range, for outputting such the packet data to the attenuation correction data creator 29. Upon inputting of the packet data having the pulse height value data of a second setup range, it outputs the packet data to the coincidence counter 25. In this embodiment, the γ-ray energy for irradiation to the examinee 14 is 662 keV, so let the first setup range be a range of from 600 keV to 680 keV. As the γ-ray energy due to the radiopharmaceutical is 511 keV, let the second setup range be a range of 450 to 530 keV. In short, the signal discriminator 28 determines or "judges" based on the pulse height value data contained in the packet data which one of the γ-ray radiated from the external radiation source 1a, 1b and the γ-ray emitted due to the PET-use radiopharmaceutical induces production of the input packet data. Based on such decision result, the signal discriminator 28 outputs the packet data to either the attenuation correction data creator 29 or the coincidence counter 25 as stated previously.

Below is an explanation as to a method for acquiring the external radiation source position information at the time point τ. The radiation source position detector 33 obtains the position information (second position information) of respective point radiation sources 2a and 2b in the circumferential direction of the opening 17 and the position information (third position information) of respective point radiation sources 2a and 2b in the axial direction of the imaging 11 (axial direction of opening 17) and determines which one of the point radiation sources 2a and 2b is emitting the γ-ray, resulting in acquisition of the position information (X) of the point radiation source of this external point radiation source that presently emits the γ-ray. More specifically the rotation angle detector 34 that is provided in the rotation driver 7 outputs to the radiation source position detector 33 a signal indicative of the rotation angle of the rotational ring 5 (namely, rotation angle detection signal). The radiation source position detector 33 obtains based on the input rotation angle detection signal the second position information of respective point radiation sources 2a and 2b. The radiation source position detector 33 is capable of obtaining, based on shift amounts of the point radiation sources 2a-2b in the axial direction of the imaging 11 by means of the linear driver, the third position information of each of point radiation sources 2a-2b in the axial direction thereof. In addition, the radiation source position detector 33 comprises a storage or memory device (not shown) which stores the relationship of the rotation angle of rotational ring 5 and the rotation angle of gear-wheel 10—i.e., rotation angle information of the radiation source holding rotational shaft 9 corresponding to the rotation angle detection signal of rotational ring 5. Upon input of the rotation angle signal from rotation angle detector 34, the radiation source position detector 33 reads the rotation angle information of the radiation source holding rotational shaft 9 corresponding to such the rotation angle signal and then determines based on this rotation angle information which one of the point radiation sources 2a and 2b presently faces the radiation release window. Whereby, the radiation source position detector 33 recognizes either one of the external radiation sources 1a-1b is radiating the γ-ray. The radiation source position detector 33 uses these information items (i.e., the second position information, the third position information, and the information indicating which one of the external radiation sources emits the γ-ray) to obtain position information (N1) of a point radiation source that is emitting its γ-ray toward the examinee 14 and then adds time information (t) to this position information (N1) for output to a point radiation source position storage device 31. The point radiation source position storage device 31 stores therein the point radiation source position information (N1) and the time information (t) as output from the radiation source position detector 33 in a correlated fashion.

The attenuation correction data creator 29 acquires, based on the detection time point τ of the packet data (N, τ, E) as input from the signal discriminator 28, the position information of point radiation source at the detection time τ from the radiation source position detector 33. An example is that when the attenuation correction data creator 29 issues a request for position information (X1) of point radiation source at a time point (t1), the radiation source position detector 33 outputs such the position information (X1) to the attenuation correction data creator 29. The attenuation correction data creator 29 uses the point radiation source position information and the detector ID contained in the packet data plus the count value of γ-ray detection signal to calculate the attenuation ratio of γ-ray at each voxel within the body of the examinee 14. The attenuation correction data creator 29 functions as an attenuation correction data creation device that forms attenuation correction data. This attenuation ratio is stored in the storage device 30 as the transmission data.

Upon acquisition of the attenuation ratio at every voxel within the body of examinee 14, the system controller opens the open/close device. Thereafter, the motor goes off, stopping the rotation of the rotational ring 5. The system controller outputs a point radiation source storage signal to the linear driver. The linear driver drives the external radiation sources 1a-1b to move in the axial direction of the opening 17, resulting in these sources being received within the radiation shield vessel 13. Whereby, the transmission imaging is completed.

The coincidence counter 25 performs coincidence count processing based on each detection time point that is included in each packet data as input from the signal discriminator 28, the packet data being for each emission signal corresponding to the above-stated paired γ-rays. More specifically, in case a difference between respective detection time points for a pair of emission signals falls within the range of a preset time window, it is decided that such paired emission signals are due to a pair of γ-rays as simultaneously produced based on the annihilation of a single positron. The coincidence counter 25 outputs, through simultaneous counting based on one pair of packet data sets for a pair of γ-rays, two detection points for detection of each γ-ray of such pair, i.e., the position information of paired radiation detectors 21, to the tomographic image information creator 26. The tomographic image information creator 26 reads the transmission data out of the storage device 30 and performs attenuation correction of the count values of emission signals. Based on the count values of these corrected emission signals and the detection point position information, the tomographic image information creator 26 creates tomographic image information. This tomographic image information is visually displayed at the display device 32.

Figure 2:
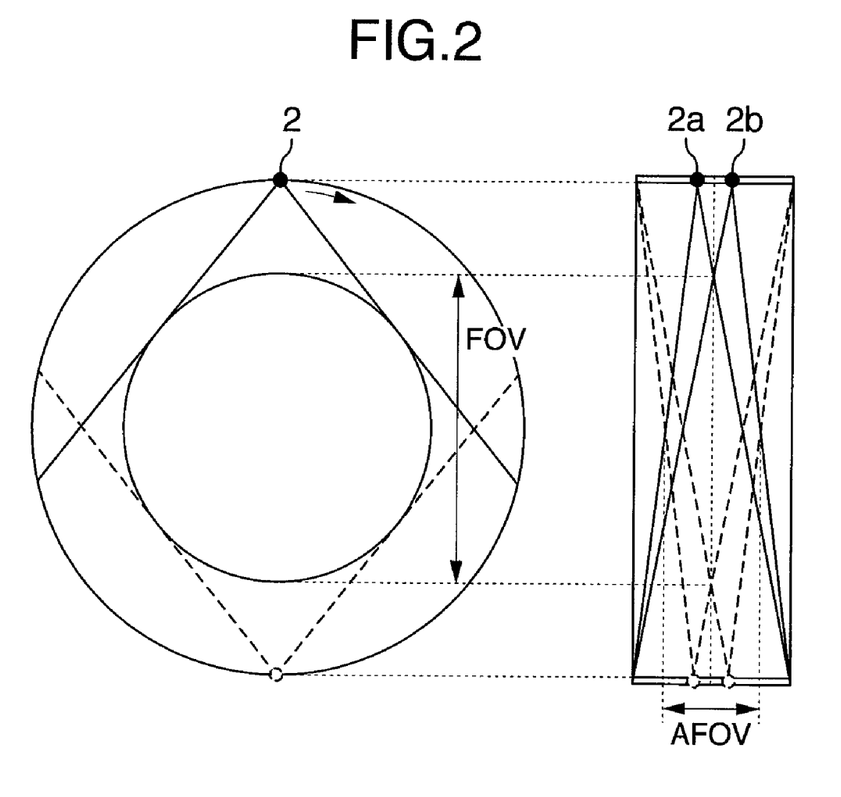
FIG. 2 is a diagram showing effective field of view (FOV) in cross-section and effective axial field of view (AFOV) in the case of using a point source of radiation.

An imaging field-of-view which is realizable when performing transmission image pickup using the external radiation sources 1a-1b of this embodiment will be described with reference to FIG. 7. In this embodiment, a coordinate axis in the horizontal direction passing through a center point O of the opening 17 is regarded as an "x" axis while letting a coordinate axis in the vertical direction penetrating the center O be a "y" axis and letting a coordinate axis in the axial direction of opening 17 be "z" axis (refer to FIGS. 6A and 6B). Major parameters indicative of the imaging field-of-view typically include an imaging field-of-view (FOV) within a longitudinal cross-sectional plane and an imaging axial field-of-view (AFOV) along the length of the bed 15 (see FIG. 2). The wider the regions of FOV and AFOV, the wider the imaging field-of-view of transmission image pickup. In this embodiment the installation range of radiation detectors 21 in the longitudinal direction of the bed 15 is represented by "d" whereas the rotation diameter of the point radiation sources 2a and 2b revolving around the examinee 14 is given as "r" (FIG. 7). Suppose that the point radiation sources 2a-2b are installed at coordinates $(z,y)=(z_s,r)$ and $(z,y)=(d-z_s,r)$ respectively in such a manner that these are symmetrically situated relative to a mid point (i.e., point with its z coordinate value of d/2) of the install range of radiation detectors 21. Using this symmetrical layout is aimed at equalization of a γ-ray irradiation area of the point radiation source 2a and that of the point radiation source 2b to thereby make respective FOVs equal to each other.

As shown in FIG. 7, the point radiation source 2a radiates a γ-ray toward inside of a region that is defined between two straight lines extending from the point radiation source 2a (on the z axis, it illuminates a line segment AD). The point radiation source 2b emits a γ-ray toward inside of a region between two straight lines extending from the point radiation source 2b (on the z axis, it illuminates a line segment EB). The coordinates of points A and B on the z axis are $A(z,y)=(z_s/2,0)$ and $B(z,y)=(d-z_s/2,0)$. AFOV may be represented by Mathematical Expression (1) below, because it is the length of a line segment AB (this is representable by a difference of z-axis coordinates of the points A and B). While FOV is different on the longitudinal cross-sectional plane of the examinee 14 along the length of bed 15, a minimal value of FOV may be given as Expression (2) below.

$$d - z_s \quad (1)$$

$$2r\left(\frac{1}{1 - z_s/d} - 1\right) \quad (2)$$

Figure 6A:
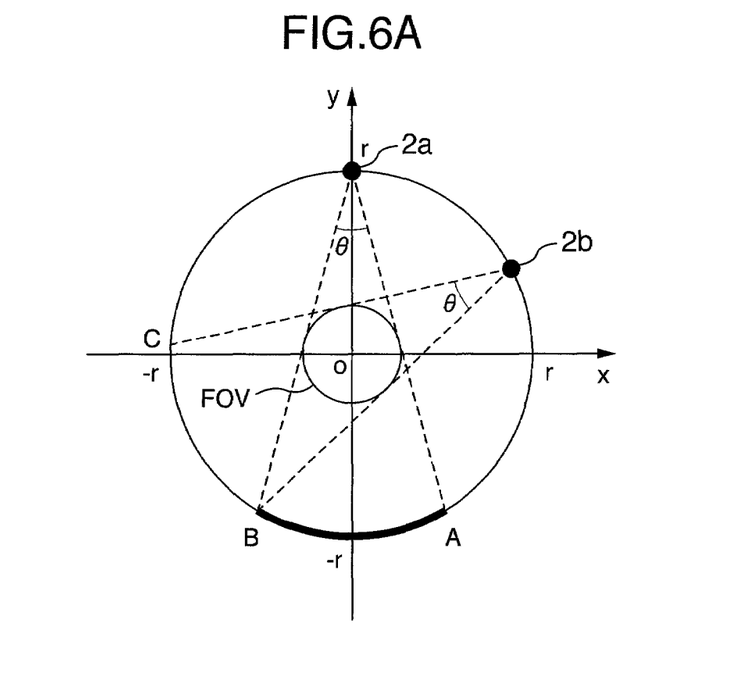
FIG. 6A is a pictorial diagram showing FOV in case point radiation sources with a fan angle of θ are disposed.
Figure 6B:
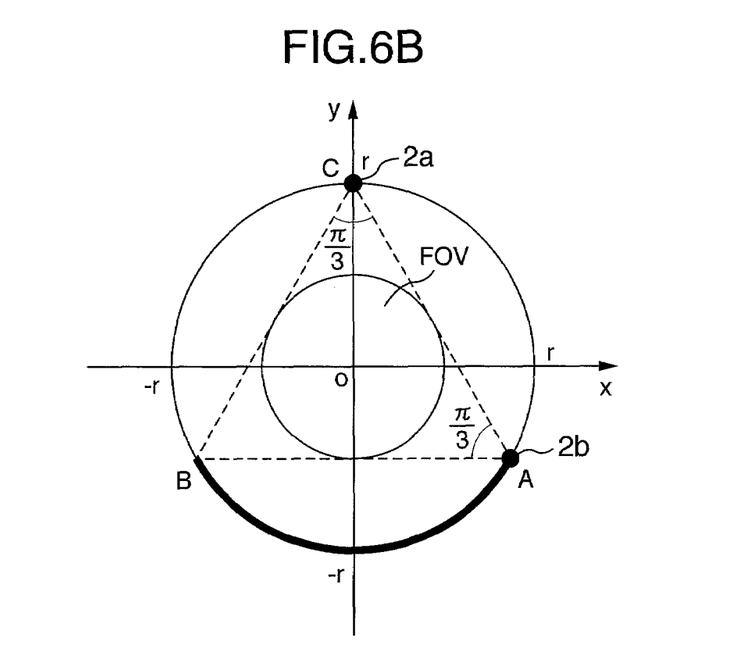
FIG. 6B is a pictorial diagram showing layout positions of the point radiation sources in case FOV becomes maximal.
Figure 7:
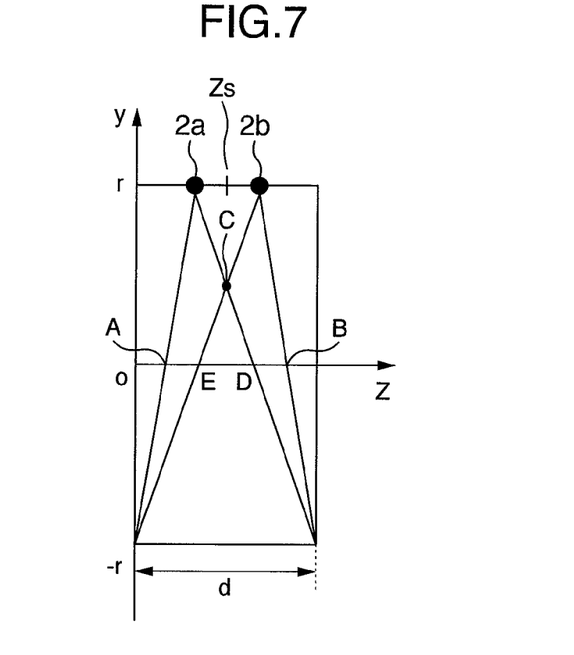
FIG. 7 is a pictorial diagram showing the layout positions of the point radiation sources shown in FIG. 1 and γ-ray release regions thereof.

Another conceivable approach to performing transmission image pickup using a plurality of external radiation sources is to use a technique for disposing two point sources of radiation within a one longitudinal plane in the circumferential direction of the opening 17 (this will be called the simple layout) and then radiating γ-rays therefrom simultaneously as shown in FIGS. 6A and 6B. In the case of the transmission imaging being carried out with the simple layout of the point radiation sources 2a-2b, a realizable imaging field-of-view is obtained for comparison with that of this embodiment.

In case the radiation detectors 21 are disposed in a ring-like form with the point radiation sources 2a-2b being placed in the simple layout, AFOV is determined by the installation range of the radiation detectors 21 disposed in the longitudinal direction of the bed 15. Additionally the FOV is determined by the fan angle θ of a conical shape of γ-ray as emitted from the point radiation source 2a, 2b and the position in the circumferential direction of the opening 17 with the point radiation sources 2a-2b being placed. However, it is necessary to dispose the external radiation source 1a, 1b in such a way as to satisfy the following conditions 1 and 2, the region of FOV being limited thereby. The condition 1 is as follows: within the radiation range of a γ-ray from the point radiation source 2a (i.e., emission range of point radiation source 2a), the other point radiation source 2b is not disposed. If the point radiation source 2b is present in the emission range of point radiation source 2a then the γ-ray from the point radiation source 2a is shielded by the radiation source housing 18A as provided at the other point radiation source 2b, resulting in failure to reach the intended radiation detector 21, thereby disabling acquisition of transmission data in such region. The condition 2 is that the point radiation sources 2a-2b do not irradiate the same region of radiation detectors 21. If γ-rays as emitted from more than two different point radiation sources fall onto the same radiation detector 21 then it is no longer possible to specify that the detected γ-ray is emitted from which one of the point radiation sources. In order to acquire the transmission data based on the information of energy of the γ-ray that passed through the examinee 14 and the position information of a point radiation source that emitted the γ-ray, in the case of failing to satisfy the condition 2, it becomes impossible to obtain the transmission data. A maximal value of FOV in the case of the point radiation sources 2a-2b being disposed to satisfy the above-stated two conditions is obtained by using the x-y coordinates shown in FIG. 6B. Letting the rotation radius of point radiation source 2a, 2b be r, the γ-ray emitted from each of them is shaped by the radiation release window to have a cone shape with a fan angle θ. The point radiation source 2a is placed at a position with its coordinate $(x,y)=(0,r)$.

The emission range of point radiation source 2a becomes an area which is surrounded by a line segment coupling the point radiation source 2a and a point A, a line segment coupling the point radiation source 2a and a point B, and an arc AB. The coordinates of the point A and point B are given as:

$$A\left(\cos\left(\frac{3}{2}\pi - \theta\right) \cdot \sin\left(\frac{3}{2}\pi - \theta\right)\right), B\left(\cos\left(\frac{3}{2}\pi + \theta\right), \sin\left(\frac{3}{2}\pi + \theta\right)\right).$$

The emission range of point radiation source 2b is an area that is surrounded by a line segment coupling the point radiation source 2b and a point C, a line segment coupling the point radiation source 2b and a point D, and an arc CD. To satisfy the condition 2, it is necessary to dispose the point radiation source 2b so that the arc CD which is the emission range of point radiation source 2b does not overlap the arc AB of the emission range of point radiation source 2a. In case the point D that is a one end of the emission range of point radiation source 2b is made identical to the point B that is one end of the emission range of point radiation source 2a (FIG. 6A), the coordinates of the point C and point D are given by:

$$C\left(\cos\left(\frac{3}{2}\pi + 3\theta\right) \cdot \sin\left(\frac{3}{2}\pi + 3\theta\right)\right), D\left(\cos\left(\frac{3}{2}\pi + \theta\right), \sin\left(\frac{3}{2}\pi + \theta\right)\right).$$

By placing the point radiation source 2b so that the point C that is one end of the emission range of point radiation source 2b is identical to the layout position of the point radiation source 2a (FIG. 6B), it is possible to satisfy the condition 1 while at the same time enabling maximization of the arc AC of the emission ranges of point radiation sources 2a-2b. In other words, when the fan angle of point radiation sources 2a-2b is θ=π/3, the arc AC becomes maximal in length, resulting FOV also being at its maximum value. FOV is representable by Expression (3). The maximum value of FOV becomes equal to r.

$$r \sin\frac{\theta}{2} \quad (3)$$

Figure 9:
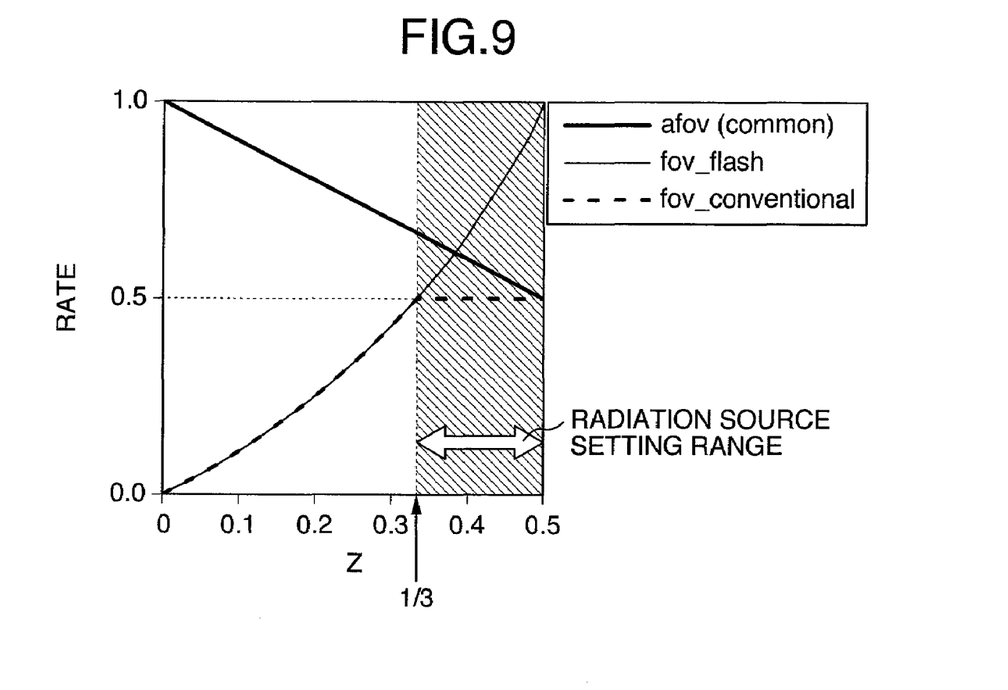
FIG. 9 is a graph for comparison of a field of view for image pickup in case two point radiation sources are simply disposed and the imaging field-of-view when using the two external point radiation sources shown in FIG. 1.

Referring to FIG. 9, comparison is made of the imaging field-of-view of transmission image pickup in the case of the simple layout of two point radiation sources 2a-2b and that in the case of this embodiment. The abscissa axis of this graph is the radiation source position regarding the axial direction z of the opening 17 in case the installation range d of radiation detectors 21 in the axial direction of the opening 17 is set to 1 (by taking account of the symmetricity of the radiation source layout, it is represented by the position of only one point radiation source, so the z's takable range is $0 \leq z \leq 0.5$). The longitudinal axis indicates the rate of practically imagable field-of-view when the maximum value (d for AFOV, and 2r for FOV) of attainable imaging field-of-view is set at 1. Since AFOV is the same in the case of using this embodiment and in the case of the simple layout, such is indicated by "AFOV (common)." Regarding FOV, let the case of using this embodiment be FOV_flash whereas the case of the simple layout is indicated by FOV_conventional. When comparing the simple layout and this embodiment for FOV, the both are the same as each other in value of the longitudinal axis in a region of less than or equal to ⅓. However, when the abscissa axis value becomes greater than ⅓, the longitudinal axis value of the simple layout is kept at a constant value (longitudinal axis is 0.5) whereas the longitudinal axis in the case of this embodiment takes a value falling within a range of from 0.5 to 1.0. To make a long story short, a wide imaging field-of-view is obtained which is one to two times greater than the maximum FOV that is obtainable by the simple layout. Practically, when the point radiation source rotation radius r is 700 mm, the FOV maximum value of the simple layout is 350 mm; in contrast, the use of this embodiment makes it possible to provide an increased range of from 350 mm to 700 mm.

According to this embodiment, it is possible to obtain advantages and effects which follow.

(1) In this embodiment, more than two point radiation sources are used while providing control for permitting radiation of γ-ray from one of these point radiation sources. Owing to this feature, it is possible to attain a wide field-of-view, thereby making it possible to shorten a time required for the transmission imaging. As the time required for the transmission imaging occupies one third of a total imaging time of PET image pickup, shortening the imaging time of the transmission imaging results in a likewise decrease in time required for PET diagnostic inspection of one examinee 14, which in turn leads to a decrease in workload of the examinee 14 while making it possible to increase the per-day inspectable number of examinees 14.

(2) As this embodiment is arranged to use a plurality of point radiation sources while providing control for permitting radiation of γ-ray from one of these point radiation sources, γ-rays as emitted from more than two different external radiation sources do not fall onto the same radiation detector 21 simultaneously. This makes it possible to accurately determine that the γ-ray detected by the radiation detector 21 is radiated from which one of the external radiation sources involved. Whereby, it is possible to accurately evaluate the attenuation quality of γ-rays within the body of examinee 14, thereby enabling achievement of higher quantitatively in γ-ray attenuation correction during emission imaging.

(3) This embodiment is arranged so that the gearwheel 10 being engaged with the rack of the internal gear 8 is rotated by rotation of the rotational ring 5, causing the radiation source holding rotational shaft 9 and the point radiation source 2a, 2b plus the shield 4a, 4b to rotate in the interior of the radiation source housing 18A, 18B. In other words, the mechanism for forcing the external radiation sources 1a-1b and radiation source housing support rod 6 and others to circulate (that is, revolves) around the opening 17 is employed to cause the radiation source holding rotational shaft 9, point radiation source 2a, 2b and shield 4a, 4b to rotate (i.e., spin) in the interior of the radiation source housing 18A, 18B. Owing to this feature, it is no longer required to provide a separate rotation mechanism for spinning the point radiation sources 2a-2b. This makes it possible to simplify the arrangement of the external radiation sources 1a-1b.

(4) In this embodiment the external radiation source 1a has the radiation source housing 18A for forming the radiation release window 3a and the point radiation source 2a plus the shield 4b, wherein the point radiation source 2a and the shield 4a are disposed within the radiation source housing 18A. Thus it is possible to control γ-ray as radiated from the point radiation source 2a in such a way as to be released out of the radiation release window 3a while being prevented from emitting in the other regions.

(5) In this embodiment the shield 4b with the point radiation source 2b being installed at its surface portion is attached via the rotation shaft 9a to the shield 4a with the point radiation source 2a being installed at a surface portion thereof, wherein this shield 4a is attached to the radiation source holding rotational shaft 9. As the radiation source holding rotational shaft 9, shield 4a, rotation shaft 9a and shield 4b are coupled respectively in this way, spinning the radiation source holding rotational shaft 9 enables simultaneous self-rotation of the point radiation source 2a and the point radiation source 2b. This avoids a need to separately provide a rotation mechanism for spinning the point radiation source 2a and a rotation mechanisms for spinning the point radiation source 2b, resulting in simplification of the configurations of external radiation sources 1a-1b.

(6) In this embodiment the point radiation source 2a that is installed at a surface portion of the shield 4a and the point radiation source 2b that is installed at a surface portion of the shield 4b are forced to spin whereby control is provided for irradiation of γ-ray from any single external radiation source. Owing to this arrangement, it is no longer necessary to provide in the external radiation sources 1a-1b shutters for control of the release of γ-rays from the external radiation sources 1a-1b. Thus the external radiation sources 1a-1b are simplified in arrangement.

(7) As this embodiment is such that the point radiation source 2a and point radiation source 2b are installed at different positions in the self-rotation direction of the radiation source holding rotational shaft 9, it is possible by permitting spinning of these point radiation sources 2a-2b to provide control for emission of γ-ray from any single one of the external radiation sources 1a-1b.

(8) In this embodiment the radiation source position detector 33 is operatively responsive to receipt of a rotation angle detection signal as output from the rotation angle detector 34 for specifying which one of the external radiation sources 1a-1b emits the γ-ray. Due to this, it becomes unnecessary to provide in any external radiation source a device for monitoring and determining which one of the external radiation sources presently radiates the γ-ray, resulting in simplification of the arrangement of external radiation sources.

(9) In this embodiment the external radiation sources 1a-1b are respectively disposed along the length of the bed 15 and arranged to revolute together around the opening 17 so that it will never happen that the other external radiation source 1b is disposed within the irradiation range of the γ-ray from the external radiation source 1a. Owing to this, the following problem does not take place: the γ-ray from the external radiation source 1a is blocked by the radiation source housing 18B or else as provided at the external radiation source 1b and thus does not reach the radiation detector(s) 21, resulting in failure of acquisition of the transmission data in such region.

(10) This embodiment is arranged so that the radiation source housing support rod 6 is attached to the rotational ring 5, wherein the rotation of this rotational ring 5 causes the external radiation source 1a, 1b to circulate around the opening 17 (examinee 14). With such an arrangement, a need is avoided to provide a rail or rails for revolution of the external radiation sources 1a-1b between the radiation detectors 21 and the opening 17. In short, a problem no longer occurs as to unwanted blockage of the γ-rays emitted from the external radiation sources 1a-1b by such rails, resulting in failure to reach the radiation detectors 21 to thereby disable acquisition of the transmission data in such region.

(11) This embodiment uses as the point radiation source 2a a single photon emission nuclear species which radiates γ-rays having an energy different from the energy of the γ-ray to be emitted due to the radiopharmaceutical that was cumulated within the body of examinee 14. This makes it possible for the PET apparatus 100 to distinguish between a γ-ray detection signal due to the γ-ray as emitted from the point radiation source 2a and a γ-ray detection signal due to the γ-ray emitted from within the body of examinee 14; thus, it is possible to reduce unwanted mixture of data between transmission and emission even when employing the post-injection method.

In this embodiment the shield 4a that is fixed to the radiation source holding rotational shaft 9 and the shield 4b fixed to the rotation shaft 9a are provided. However, it is also permissible to avoid the use of such shields 4a-4b and employ an arrangement using a material having its function of shielding an entirety of the radiation source holding rotational shaft 9. In this case also, similar advantages to those of this embodiment are obtainable.

Embodiment 2

A radiological imaging apparatus in accordance with another embodiment of this invention will be described while referring to the accompanying drawings. The radiological imaging apparatus of this embodiment will be explained by taking as an example a PET apparatus having three external radiation sources using $^{137}$Cs (cesium 137) that is a single photon emission nuclear species.

The PET apparatus 100A of this embodiment has an arrangement which replaces the external radiation sources 1a-1b in the PET apparatus 100 of the embodiment 1 by external radiation sources 1c, 1d and 1e. The external radiation source 1c has a radiation source housing 18C, a transmission-use point radiation source ($^{137}$Cs, to be referred to as point radiation source hereinafter) 2c, and a shield 4c. The external radiation source 1d has a radiation source housing 18D, a point radiation source of $^{137}$Cs 2d and a shield 4d. The point radiation source 2d that is provided at a surface portion of the shield 4d is disposed at a position being 120-degree offset relative to the point radiation source 2c in the rotation direction of the radiation source holding rotational shaft 9. The external radiation source 1e has a radiation source housing 18E, a $^{137}$Cs point radiation source 2e and a shield 4e. The point radiation source 2e that is provided at a surface portion of the shield 4e is placed at a location being 120°-shifted relative to the point radiation source 2d in the rotation direction of radiation source holding rotational shaft 9. The point radiation source 2c that is provided at a surface portion of the shield 4c is situated at a position being 120°-shifted relative to the point radiation source 2e in the rotation direction of radiation source holding rotational shaft 9. The remaining parts of the PET apparatus 100A are similar to those of the PET apparatus 100. In this embodiment also, a γ-ray is emitted from any one of the external radiation sources 1c, 1d and 1e at a time.

The imaging field-of-view which is realizable when performing transmission image pickup using the external radiation sources 1c, 1d and 1e of this embodiment will be described. In this embodiment, a coordinate axis in the horizontal direction passing through a center point O of the opening 17 is regarded as an x axis while letting a coordinate axis in the vertical direction penetrating the center O be y axis and letting a coordinate axis in the axial direction of opening 17 be z axis. In this embodiment the installation range of radiation detectors 21 along the length of the bed 15 is given as d while letting the rotation radius of circulation of the point radiation source 2c, 2d, 2e around an examinee 14 be r (see FIG. 8). The point radiation source 2d is disposed at a mid point (i.e., point with its z coordinate of d/2) of the installation range of radiation detectors 21; the point radiation source 2c, 2e are symmetrically laid out with the point radiation source 2d being as the center therebetween. Using this symmetrical layout makes it possible to achieve equalization of γ-ray radiation regions of the point radiation sources 2c-2e, thereby enabling each to be equal in FOV to the others.

Figure 8:
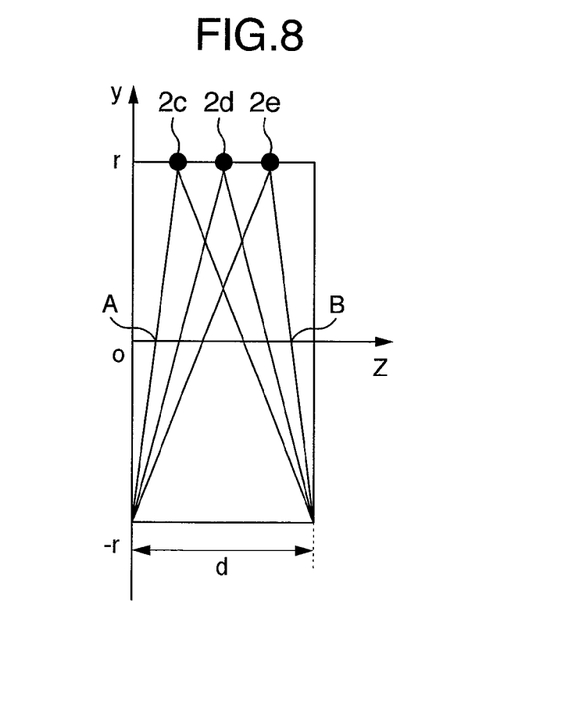
FIG. 8 is a pictorial diagram showing layout positions of point radiation sources of PET apparatus which is another embodiment of this invention and γ-ray release regions thereof.

As shown in FIG. 8, the point radiation source 2c radiates a γ-ray toward inside of a region which is defined between two straight lines extending from the point radiation source 2c. The point radiation source 2d emits a γ-ray toward inside of a region that is between two straight lines extending from the point radiation source 2d. The point radiation source 2e gives off a γ-ray toward inside of a region between two straight lines extending therefrom. In brief, the point radiation source 2c, 2d, 2e radiates γ-ray to a line source AB on Z axis. The coordinates of points A and B on Z axis are A($z_s$/2,0) and B(d−$z_s$/2,0). AFOV is the length of line segment AB and thus is representable by Expression (4) below. FOV may be given by d−$z_s$. Although FOV is different on the longitudinal cross-sectional plane of the examinee 14 along the length of the bed 15, the minimum value of FOV may be represented as Expression (5) below.

$$d - z_s \quad (4)$$

$$2r\left(\frac{1 + 2(z_s/d)}{3 - 2(z_s/d)}\right) \quad (5)$$

In case γ-rays are simultaneously radiated from three point radiation source 2c, 2d, 2e which are simply disposed in the circumferential direction of opening 17 within the imaging 11, a realizable imaging field-of-view is obtained for comparison to the imaging field-of-view of this embodiment. In the case of the point radiation sources 2c-2e being simply disposed to satisfy the above-noted conditions 1 and 2, FOV is representable by Expression (3) in a similar way to the embodiment 1. Thus the maximum value of FOV becomes r.

Figure 10:
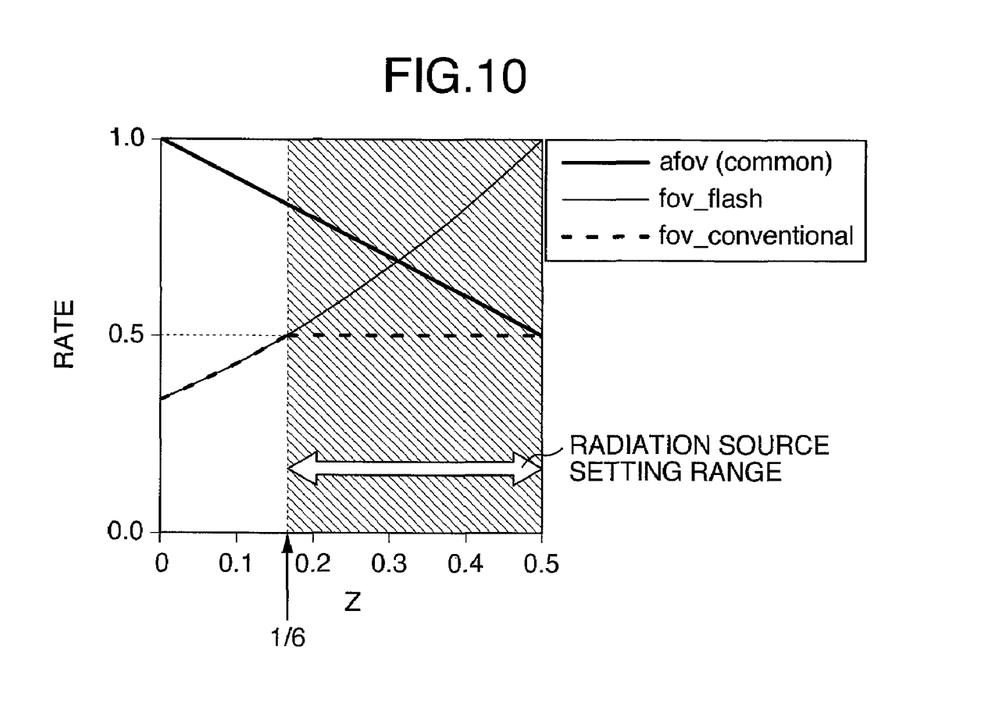
FIG. 10 is a graph for comparison of an imaging field-of-view in case three point radiation sources are simply laid out and the imaging field-of-view when using three external point radiation sources in accordance with another embodiment of this invention.

Using FIG. 10, comparison is made of the transmission imaging field-of-view in the case of the simple layout of three point radiation sources 2c, 2d and 2e and that in the case of this embodiment. The abscissa axis of this graph is the radiation source position as to the long-side direction z of the bed 15 in case the installation range d of radiation detectors 21 along the length of bed 15 is set at 1 (in light of the symmetricity of the radiation source layout, it is represented by the position of only one radiation source, so the z's takable range is $0 \leq z \leq 0.5$). The longitudinal axis indicates the rate of really imagable field-of-view when the maximum value (d for AFOV, and 2r for FOV) of attainable imaging field-of-view is set to 1. Because of the fact that AFOV is the same in the case of using this embodiment and in the case of the simple layout, this is indicated by AFOV(common). Regarding FOV, let the case of using this embodiment be FOV_flash, while the case of the simple layout is given as FOV_conventional. As in the embodiment 1, according to this embodiment, it is possible to obtain, in a region with the abscissa axis value becoming equal to ⅙ or greater, a wide imaging field-of-view that is one to two times greater than that of the simple layout.

According to this embodiment, it is possible to obtain the above-stated advantages (1) to (11) attainable in the embodiment 1.

Although in the first embodiment and second embodiment the point radiation sources are comprised of $^{137}$Cs, this may be replaced by any one as selected from the group consisting of $^{57}$Co (cobalt 57), $^{99m}$Tc (technetium 99m), $^{123m}$Te (tellurium 123m), $^{139}$Ce (cerium 139), $^{153}$Gd (gadolinium 153), $^{241}$Am (americium 241), and $^{22}$Na (sodium 22).

While in the first and second embodiments the explanation thereof are given while taking as an example the emission/transmission simultaneous collection method (ET coincidence collection method) which performs both the transmission imaging and the emission imaging at a time, the same may also be applicable to post-injection methods for continuous execution of the transmission imaging and the emission imaging.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A radiological imaging apparatus, comprising:
an imaging apparatus with an opening being formed for insertion of a bed thereinto; and
an attenuation correction data creation device,
wherein said imaging apparatus includes a plurality of radiation detectors disposed around said opening and a plurality of gamma ray generation means residing between said opening and said radiation detectors as placed at a position nearest to said opening and being disposed in a longitudinal direction of said bed,
wherein said plurality of gamma ray generation means respectively comprises gamma ray sources each being a single photon emission nuclear species and being arranged to alternately radiate a gamma ray from any one of said gamma ray generation means to its outside in propagation for said opening,
wherein said attenuation correction data creation device is operative to create attenuation correction data based on a detection signal as output from said radiation detectors due to incoming radiation of the gamma ray to be emitted from said gamma ray generation means.
wherein each said gamma ray generation means has a housing which is a radiation shield surrounding said gamma ray source, and wherein said housing forms a release window for releasing said gamma ray emitted from said gamma ray source toward said opening; and
the radiological imaging apparatus further comprising:
a support member for supporting a plurality of housings each being similar in structure to said housing;
a rotator with said support member being attached thereto, for rotating to thereby cause said support member to circulate around said opening; and
a radiation source holding member with said gamma ray source attached thereto, for rotating within said housing to permit said gamma ray from said gamma ray source to travel toward said opening.

2. The radiological imaging apparatus according to claim 1, further comprising:
a drive device for performing rotation driving of said rotator;
an internal gear with a rack being formed therein; and
a gearwheel provided at said radiation source holding member for being engaged with said rack and rotatable due to the rotation of said rotator.

3. The radiological imaging apparatus according to claim 1, wherein respective one of said plurality of gamma ray sources are disposed at different positions in the rotation direction of said radiation source holding member.

4. The radiological imaging apparatus according to claim 1, further comprising:
a radiation shield provided at said radiation source holding member for shielding, when said point radiation source is at a position other than said release window, a gamma ray emitted from said point radiation source to thereby prevent it from being radiated from said release window.

* * * * *